US00PP35083P3

(12) United States Plant Patent
Dixon et al.

(10) Patent No.: US PP35,083 P3
(45) Date of Patent: Apr. 4, 2023

(54) ***CANNABIS* PLANT NAMED 'RED KROSS02-BK'**

(50) Latin Name: ***Cannabis* hybrid**
Varietal Denomination: Red KROSS02-BK

(71) Applicant: Pharmers Group LLC, Elk Grove, CA (US)

(72) Inventors: Ian Dixon, Elk Grove, CA (US); Stephen King, Jr., Elk Grove, CA (US)

(73) Assignee: Ian Dixon, Elk Grove, CA (US)

( * ) Notice: Subject to any disclaimer, the term of this patent is extended or adjusted under 35 U.S.C. 154(b) by 0 days.

(21) Appl. No.: 17/300,683

(22) Filed: Sep. 23, 2021

(65) Prior Publication Data

US 2022/0104421 P1 Mar. 31, 2022

Related U.S. Application Data

(60) Provisional application No. 63/085,930, filed on Sep. 30, 2020.

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
CPC ..... A01H 6/28; A01H 5/02; A01H 5/12
See application file for complete search history.

*Primary Examiner* — Keith O. Robinson

(57) ABSTRACT

The unique annual herbaceous *Cannabis* plant variety 'Red KROSS02-BK' is provided. The variety can be distinguished by its outstanding features as described.

4 Drawing Sheets

Latin name of the genus and species: Genus—*Cannabis*. Species—hybrid.

Variety denomination: The new *Cannabis* plant claimed is of the variety denominated 'Red KROSS02-BK'.

BACKGROUND OF THE INVENTION

The present invention relates to a new and distinct annual variety of a *Cannabis* hybrid, which has been given the variety denomination of 'Red KROSS02-BK'. 'Red KROSS02-BK' is intended for use in industrial applications, for example, as a source of fiber, pulp, biomass, seed, and seed oils that serve as raw material for textiles; paper products; construction materials; animal forage; dietary supplements; and/or cannabinoid extracts, distillates, and isolates.

SUMMARY OF THE INVENTION

The new variety was developed from plants initially produced from the open pollination of the hybrid variety 'Ringo's Gift' (not patented) by a hemp hybrid variety known as 'Red Kross' (not patented) that is the F1 offspring of the hemp hybrid varieties 'Baox' (not patented) and 'Finola' (not patented). After pollination, F1 seed was collected and subsequently planted on a 20-acre plot.

Successive, multiple family group selection was carried out in order to decrease harvest time to 80-100 days, increase stem productivity and fiber content, and decrease the content of tetrahydrocannabinol (THC) compounds while keeping cannabidiol (CBD) levels above 10%. Selection by anatomic structure of cross section of the stem and high terpene profiles in the flowering stage was also included.

100 self-pollinated F2 plants were selected based on vigor and desirable phenotypic characteristics. This initial selection was followed by a second selection of 5 plants from among the 100 plants initially selected. The 5 plants were allowed to self-pollinate, and F2 seed was collected and then grown on a 1-acre plot. Cannabinoid profiles of F2 plants were tested, and the new variety was selected as a single plant.

A phytochemical profile characterized by ultralow or undetectable levels of all cannabinoid compounds except for cannabidiolic acid (CBD-A), specifically undetectable levels of the cannabinoid compounds: cannabigerolic acid (CBG-A), cannabigerol (CBG), CBD, Δ9-tetrahydrocannabinolic acid (THC-A), Δ9-tetrahydrocannabinol (Δ9-THC), Δ8-tetrahydrocannabinoil (Δ8-THC), Δ10-tetrahydrocannabinol (Δ10-THC), cannabichromenic acid (CBC-A), cannabichromene (CBC), cannabigerovarinic (CBGV-A), cannabidivarinic acid (CBDV-A), cannabidivarin (CBDV), tetrahydrocanabivarinic acid (THCV-A), tetrahydrocannabivarin (THCV), cannabichromevarinic acid (CBCV-A), cannabinol (CBN), cannabicyclol (CBL), and cannabinodiolic acid (CBND-A); cannabidiolic acid (CBD-A) levels under 10% w/w; and total cannabinoid levels under 10% w/w.

TABLE 1

Exemplary Profile of Key Cannabinoids.

| Analyte | LOD | LOQ | Result (% w/w) | Result (mg/gm) |
|---|---|---|---|---|
| THCa | 0.012 | 0.038 | ND | ND |
| Δ9-THC | 0.014 | 0.042 | ND | ND |
| Δ8-THC | 0.012 | 0.037 | ND | ND |
| THCV-A | 0.010 | 0.030 | ND | ND |
| THCV | 0.012 | 0.036 | ND | ND |
| CBD-A | 0.004 | 0.012 | 6.091 | 60.91 |
| CBD | 0.012 | 0.038 | ND | ND |
| CBDV-A | 0.006 | 0.018 | ND | ND |
| CBDV | 0.007 | 0.020 | ND | ND |
| CBN-A | 0.010 | 0.031 | ND | ND |

TABLE 1-continued

Exemplary Profile of Key Cannabinoids.

| Analyte | LOD | LOQ | Result (% w/w) | Result (mg/gm) |
|---|---|---|---|---|
| CBN | 0.009 | 0.028 | ND | ND |
| CBG-A | 0.008 | 0.023 | ND | ND |
| CBG | 0.014 | 0.042 | ND | ND |
| CBC-A | 0.005 | 0.016 | ND | ND |
| CBC | 0.014 | 0.043 | ND | ND |
| CBL-A | 0.007 | 0.020 | ND | ND |
| CBL | 0.018 | 0.054 | ND | ND |
| Total | | | 6.091 | 60.91 |

*Total THC = (THCA * 0.877) + THC (i.e., delta 9 THC) + delta 8 THC; LOD = Limit of Detection; LOQ = Limit of Quantitation

TABLE 2

Exemplary Profile of Key Cannabinoids.

| Analyte | Amount | Amount | LOD/LOQ (mg/g) |
|---|---|---|---|
| CBC | ND | ND | 1.075/3.224 |
| CBCA | <1 mg/g | <1 mg/g | 2.408/7.224 |
| CBD | 1.053% | 10.53 mg/g | 1.180/3.539 |
| CBDA | 8.306% | 83.06 mg/g | 0.977/2.930 |
| CBDV | ND | ND | 1.671/5.014 |
| CBDVA | ND | ND | 1.313/3.939 |
| CBG | ND | ND | 2.242/6.727 |
| CBGA | 0.740% | 7.40 mg/g | 2.138/6.415 |
| CBL | ND | ND | 0.786/2.358 |
| CBN | ND | ND | 0.857/2.570 |
| CBNA | ND | ND | 3.130/9.390 |
| $\Delta^8$-THC | ND | ND | 1.401/4.203 |
| $\Delta^9$-thc | ND | ND | 1.286/3.859 |
| THCA | <1 mg/g | <1 mg/g | 1.364/4.093 |
| THCV | ND | ND | 1.176/3.529 |
| THCVA | ND | ND | 1.155/3.464 |
| Moisture | 9.709 | | |
| TOTAL THC | <1 mg/g | <1 mg/g | |
| TOTAL CBD | 8.337% | 83.37 mg/g | |
| TOTAL CANNABINOIDS | 10.099% | | |

TOTAL THC = (THCA × 0.877) + THC
TOTAL CBD = (CBDA × 0.877) + CBD
DRY-WEIGHT AMOUNTS SHOWN

Multiple clones of the selected plant were created. For the cloning reproduction, all clones were taken on the same day, Dec. 5, 2020. A single mother plant of the new variety produced 150 'Red KROSS02-BK' clones, ensuring genetic homogeneity of experimental plants, which became second-stage mother (M2) plants. Subsequently, a total of 500 'Red KROSS02-BK' clones were taken from 100 M2 plants, 5 clones from every M2 plant. Branches, 20 cm long, were initially cut from M2 plants with a pair of pruning shears and were placed in water and 5 ml of 5% hydrogen peroxide until the application of treatments described below. Cut clones were stripped of lower fan leaves using pruning shears, and then were re-cut at a 45° angle to a 15 cm length. The ends of each leaf were cut in order to promote new growth. The bottom of each clone stem was then dipped in a root stimulant and inserted in a substrate with the stem tip approximately 1.5 cm from the plug base and placed into a seedling tray. The trays were covered with 7" humidity domes with closed vents, and were placed on their appropriate table on a Hydro farm seedling heat mat. The following characteristics of the new variety have been repeatedly observed in each of the clones and can be used to distinguish 'Red KROSS02-BK' as a new and distinct variety of *Cannabis:*

1. A phytocannabinoid profile characterized by
   a. Undetectable levels of the cannabinoid compounds cannabigerolic acid (CBG-A), cannabigerol (CBG), CBD, Δ9-tetrahydrocannabinolic acid (THC-A), Δ9-tetrahydrocannabinol (Δ9-THC), Δ8-tetrahydrocannabinoil (Δ8-THC), Δ10-tetrahydrocannabinol (Δ10-THC), cannabichromenic acid (CBC-A), cannabichromene (CBC), cannabigerovarinic (CBGV-A), cannabidivarinic acid (CBDV-A), cannabidivarin (CBDV), tetrahydrocanabivarinic acid (THCV-A), tetrahydrocannabivarin (THCV), cannabichromevarinic acid (CBCV-A), cannabinol (CBN), cannabicyclol (CBL), and cannabinodiolic acid (CBND-A);
   b. cannabidiolic acid (CBD-A) levels under 10% w/w;
   c. total cannabinoid levels under 10% w/w; and
2. an autoflowering vs. photoperiod reproductive cycle.

Plants of the new variety differ from plants of the seed parent 'Ringo's Gift' and from the pollen parent 'Red Kross' in their phytochemical content. In particular, 'Red KROSS02-BK' differs from both parent strains in that it has ultralow or non-detectable levels of all cannabinoid compounds except for cannabidiolic acid (CBD-A), cannabidiolic acid (CBD-A) levels under 10% w/w, and total cannabinoid levels under 10% w/w. These differences make the new variety especially desirable for industrial uses because a phytocannabinoid profile that lacks psychoactive cannabinoids exempts the plant material and oil extracts from prohibitions imposed by the Controlled Substances Act and greatly reduces or eliminates the need to remediate extracts to remove psychoactive cannabinoids. Production costs and efficiency are thereby greatly improved, making the variety especially useful and desirable for industrial applications such as preparing CBD-A isolate.

BRIEF DESCRIPTION OF THE DRAWINGS

The accompanying photographic illustrations show the typical appearance of the new variety 'Red KROSS02-BK'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
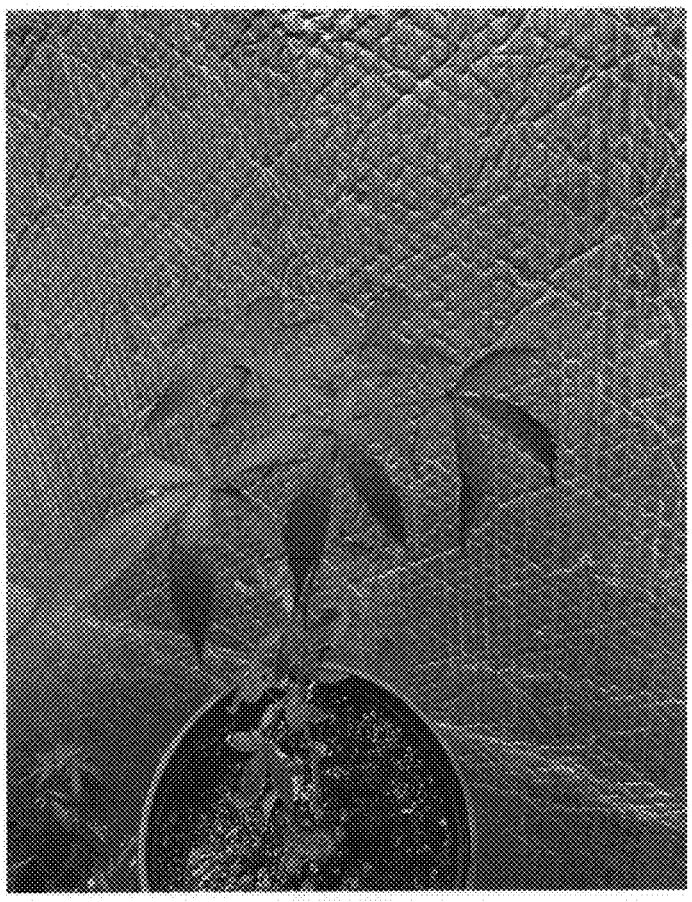
FIG. 1 is a photograph of the new variety 'Red KROSS02-BK', at 6 weeks.
Figure 2:
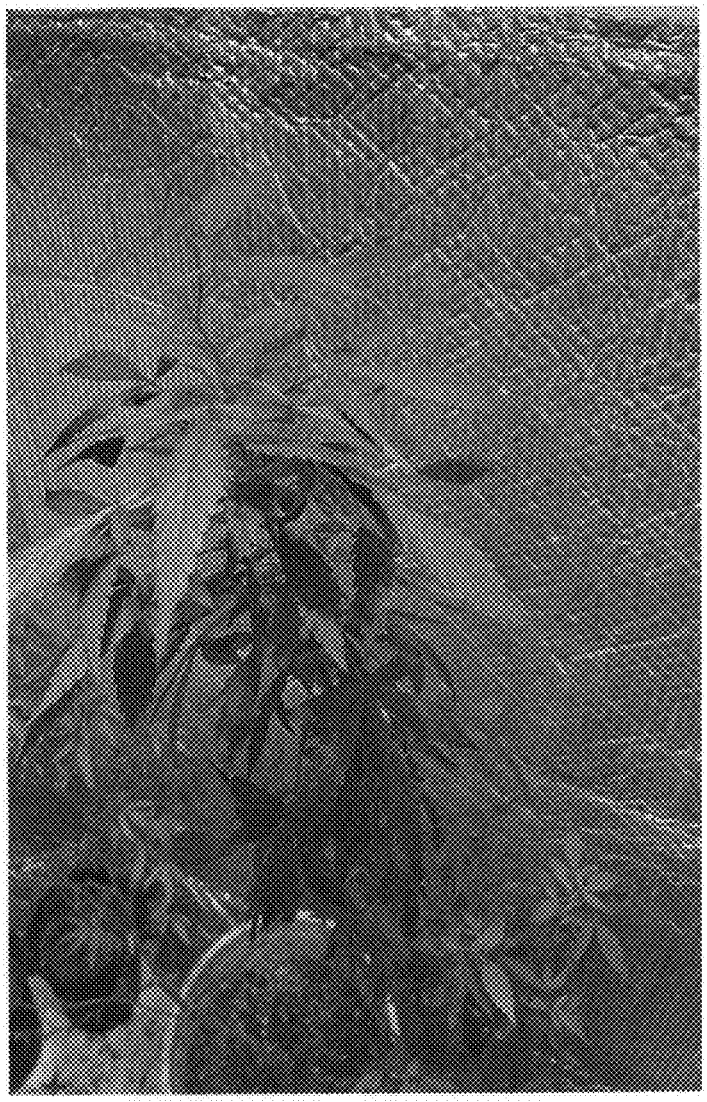
FIG. 2 is a photograph of a fully-grown mother plant of new variety 'Red KROSS02-BK'.
Figure 3:
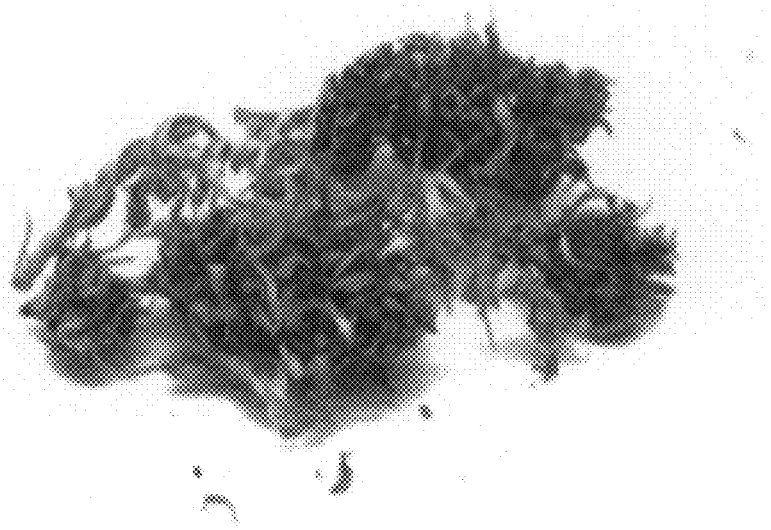
FIG. 3 is a photograph of new variety 'Red KROSS02-BK' as dry flower.
Figure 4:
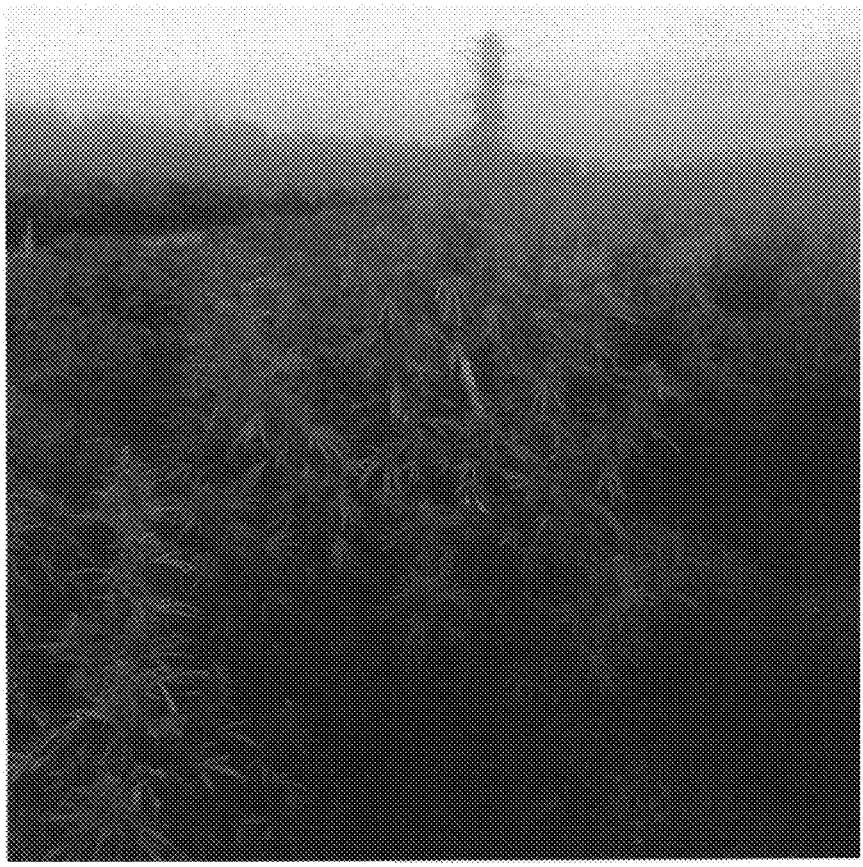
FIG. 4 is a photograph of new variety 'Red KROSS02-BK' at 100 days grown in a field.

The following detailed description sets forth the distinctive characteristics of 'Red KROSS02-BK'. The data which define these characteristics were collected from asexual reproductions of the original selection. Dimensions, sizes, colors, and other characteristics are approximations and averages set forth as accurately as possible. The plant history was taken on plants approximately 4 months of age, and the descriptions relate to plants grown in Rio Oso, Calif., U.S.A. Color notations are in reference to the standard digital hexadecimal color and RGB color numbering system known to those of ordinary skill in color designation and color matching.

Type: Herbaceous tap-rooted annual.

Classification:

*a. Family.*—Cannabaceae.
*b. Genus.*—*Cannabis.*
*c. Species.*—Hybrid.
*d. Common name.*—Hemp.

Parentage: Hemp hybrid variety 'Ringo's Gift' and hemp hybrid variety 'Red Kross', a hemp hybrid cross of the hemp varieties 'Baox' and 'Finola'.

PLANT

General:

*a. Parentage.*—i. Male parent — 'Red Kross' hybrid hemp variety, the offspring of hybrid hemp varieties Baox (a hybrid hemp variety) and Finola (an autoflowering hybrid hemp variety). ii. Female parent — 'Ringo's Gift' hybrid hemp variety.
*b. Average height.*—3-4 feet.
*c. Average spread.*—5-6 feet.
*d. Productivity.*—1.5 lbs/plant.
*e. Fragrance.*—Fruity, melon-like.
*f. Proportion of hermaphrodite plants.*—Low.
*g. Proportion of female plants.*—100%.
*h. Proportion of male plants.*—0%.
*i. Type of inflorescence.*—Racemose.
*j. Photoperiodicity.*—Autoflowering.
*k. Disease resistance/susceptibility.*—Very Strong Disease Resistance.
*l. Hardiness.*—Impeded growth under 45 degrees Fahrenheit.

STEM

General:

*a. Shape.*—Oval.
*b. Average length of internode.*—22 cm.
*c. Depth of grooves.*—Medium.
*d. Pith in cross section.*—Medium.
*e. Trichome type.*—Bulbous.
*f. Color.*—Dark green (Hex: #00A877 hue/color group: Green; color name: Munsell RGB: 0,168,119).
*g. Average diameter.*—15 cm.
*h. Average length.*—20 cm.

LEAF

General:

*a. Leaf color* (*top side*).—Dark green (Hex: #00A877; hue/color group: Green; color name Munsell; RGB: 0,168,119).
*b. Leaf color* (*bottom side*).—Medium dark green (Hex: #586B41 hue/color group: Green; color name Chalet Green; RGB: 88,107,65.
*c. Number of leaflets per leaf.*—Many (>7).
*d. Central leaflet length mean.*—20 cm.
*e. Central leaflet width mean.*—20 cm.
*f. Margin.*—Coarsely serrated, dentate.
*g. Apex.*—Elongated, pointed, thin.
*h. Base.*—Palmated.

PETIOLE

General:

*a. Length.*—Long (8 mm-12 mm).
*b. Anthocyanin intensity.*—Medium.
*c. Diameter.*—4-7 mm.
*d. Strength.*—Strong.
*e. Texture.*—Smooth to gritty depending on plant size and maturity.
*f. Color.*—Blue Gray (Hex: #7FACBE hue/color group: Blue; color name Glacier; RGB: 127,172,190.

FEMALE FLOWER

General:

*a. Natural flowering season.*—Autoflowering.
*b. Number of petals per flower.*—5-7.
*c. Pistil.*—i. Number per flower — 2 per bract. ii. Length. — 0.6 cm avg.
*d. Involucral bract.*—i. Length — 0.4 cm avg.
*e. Stipule.*—i. Length — 0.6 cm avg. ii. Diameter — 0.1-0.2 cm. iii. Shape — Pointed, blade like, thin. iv. Texture — Smooth. v. Color — Dark green (#3A5116 hue/color group: Green; color name: Verdun Green; RGB: 58,81,22).
*f. Stigma.*—i. Shape — Acute. ii. Diameter — 0.6 cm avg. iii. Color — Medium dark brown; Hex: #6F5A3C hue/color group: Yellow; color name: Yellow Metal; RBG: 111,90,60.
*g. Style.*—i. Length — 0.3-0.6 cm. ii. Color — Green-cyan (Hex: #3B5A4E hue/color group: Green; color name: Plantation; RGB: 59,90,78).
*h. Ovary.*—i. Color — Dark green (Hex: #3A5116 hue/color group: Green; color name Verdun Green; RGB: 58,81,22).
*i. Natural flowering season.*—Early (60 days).
*j. Tepal.*—i. Presence of anthocyanin — Very strong.

SEEDS

General:

*a. Shape.*—Ovate/Oblong.
*b. Weight per* 1000 *seeds.*—13 g.
*c. Color of testa.*—Grey-Brown (Hex #726139 hue/color group: Brown; color name Shingle; RGB: 114,97,57).
*d. Marbling.*—Strong.
*e. Size.*—2.2 mm-3.2 mm.

What is claimed is:

1. A new and distinct variety of *Cannabis* plant named 'Red KROSS02-BK', as illustrated and described herein.

* * * * *